(12) United States Patent
Lubock et al.

(10) Patent No.: US 7,945,307 B2
(45) Date of Patent: May 17, 2011

(54) MARKER DELIVERY SYSTEM WITH OBTURATOR

(75) Inventors: Paul Lubock, Laguna Niguel, CA (US); Richard Quick, Mission Viejo, CA (US)

(73) Assignee: Senorx, Inc., Irvine, CA (US)

( * ) Notice: Subject to any disclaimer, the term of this patent is extended or adjusted under 35 U.S.C. 154(b) by 634 days.

(21) Appl. No.: 11/499,466

(22) Filed: Aug. 4, 2006

(65) Prior Publication Data

US 2008/0033280 A1    Feb. 7, 2008

(51) Int. Cl.
*A61B 5/05* (2006.01)
(52) U.S. Cl. ............ 600/414; 600/410; 604/103.1; 606/213; 128/899
(58) Field of Classification Search .................. None
See application file for complete search history.

(56) References Cited

U.S. PATENT DOCUMENTS

| | | | |
|---|---|---|---|
| 5,800,389 A * | 9/1998 | Burney et al. ............ 604/164.01 |
| 5,845,646 A * | 12/1998 | Lemelson ..................... 128/899 |
| 6,613,002 B1 * | 9/2003 | Clark et al. .................... 600/593 |
| 6,862,470 B2 * | 3/2005 | Burbank et al. ............... 600/431 |
| 6,939,318 B2 * | 9/2005 | Stenzel ........................... 604/60 |
| 2003/0236573 A1 | 12/2003 | Evans et al. |

FOREIGN PATENT DOCUMENTS

| EP | 1 114 618 A | 7/2001 |
|---|---|---|
| WO | WO 02/41786 | 5/2002 |

OTHER PUBLICATIONS

International Search Report for PCT/US2007/016918 mailed Nov. 26, 2007.
Written Opinion of the International Searching Authority for PCT/US2007/016918 mailed Nov. 26, 2007.

\* cited by examiner

*Primary Examiner* — Unsu Jung
*Assistant Examiner* — Nigel Fontenot

(57) ABSTRACT

A marker delivery device is described which has an obturator with an elongated shaft, an inner lumen, a proximal end, and a substantially sealed distal end. One or more tissue markers are deployed within the inner lumen of the elongated shaft of the obturator. Preferably, the tissue marker(s) is disposed within an inner lumen of a marker delivery tube which is disposed within the inner lumen of the elongated shaft of the obturator. The marker delivery tube has an opening for discharging the tissue markers into a body (e.g. biopsy) cavity. The distal tip of the marker delivery tube is configured to penetrate the substantially sealed distal end of the obturator so that tissue markers can be delivered while the obturator is in place within the body. Preferably, the obturator includes a detectable element capable of producing a relatively significant image signature during MRI.

3 Claims, 8 Drawing Sheets

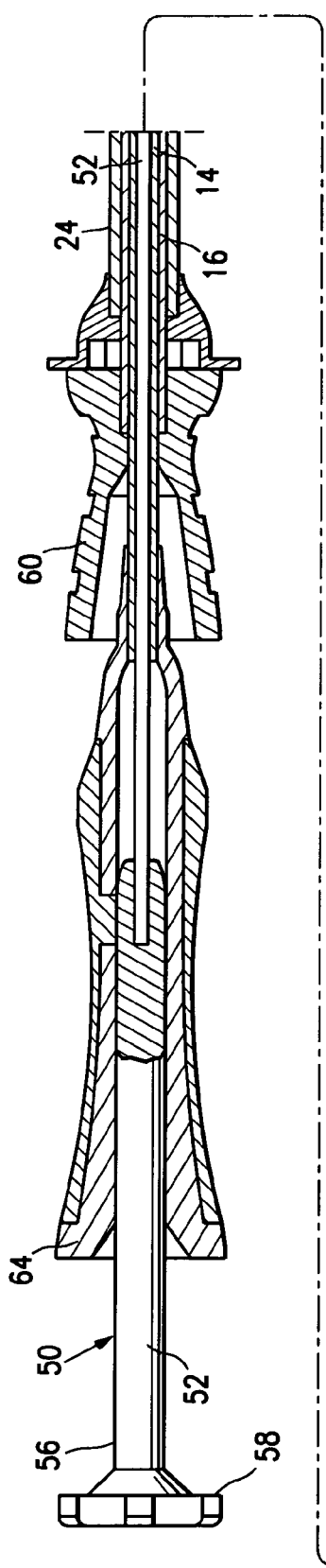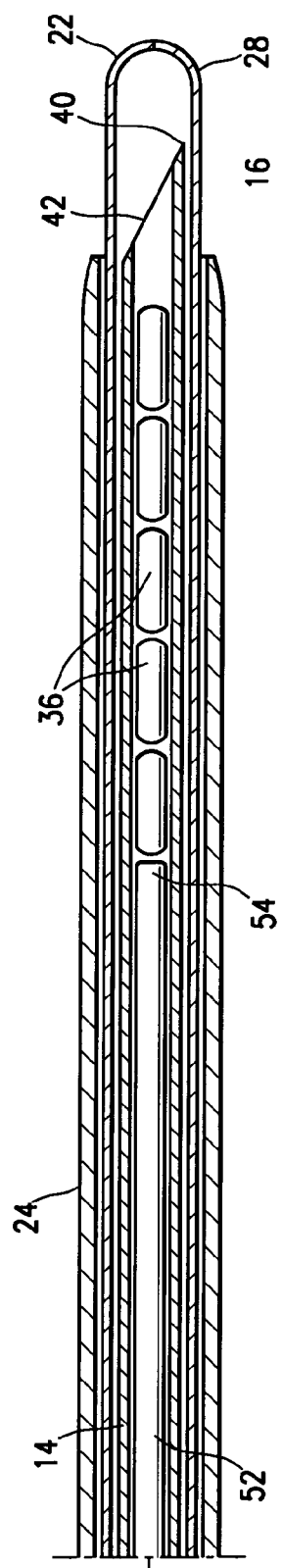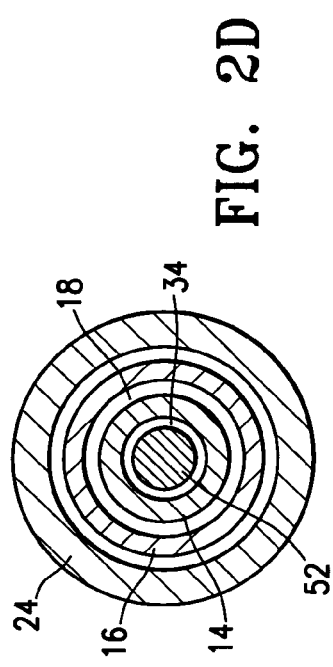
FIG. 2C
FIG. 2D

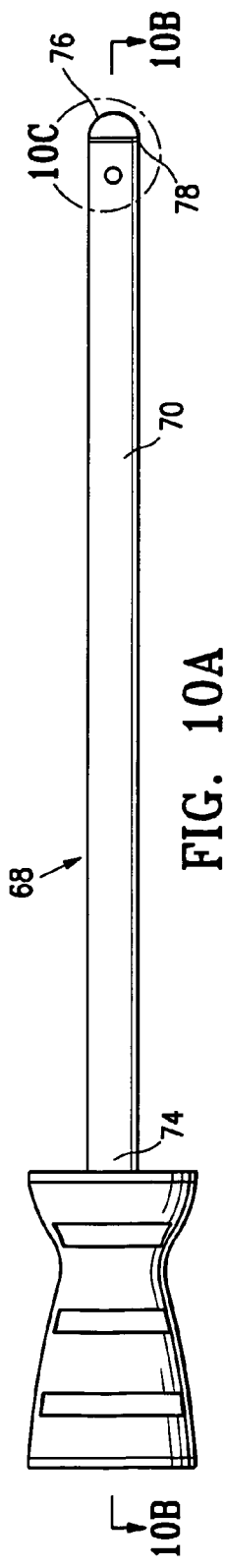
FIG. 10A
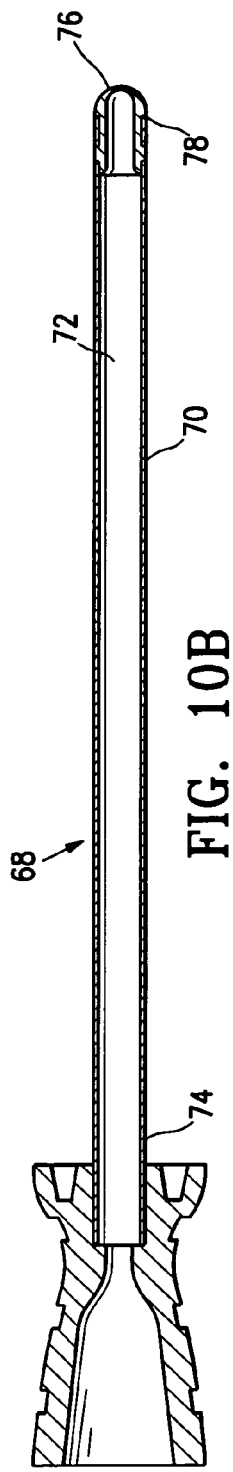
FIG. 10B
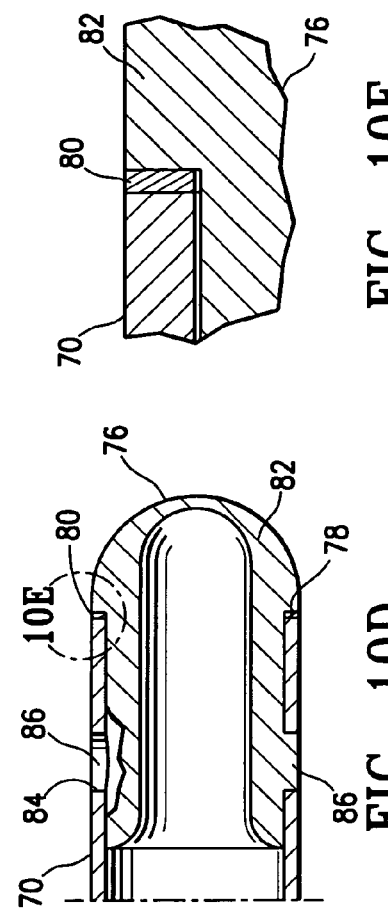
FIG. 10E
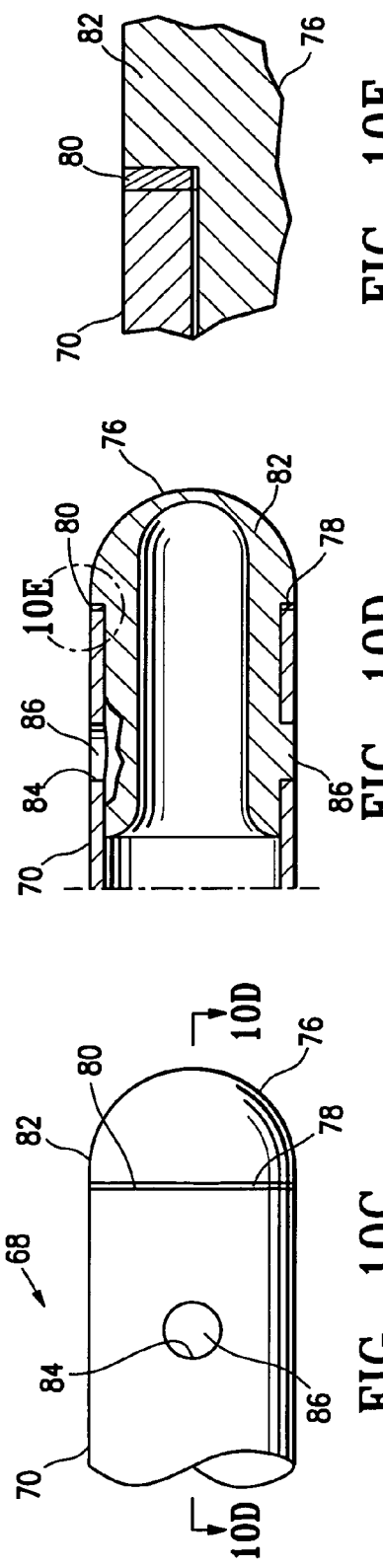
FIG. 10D
FIG. 10C

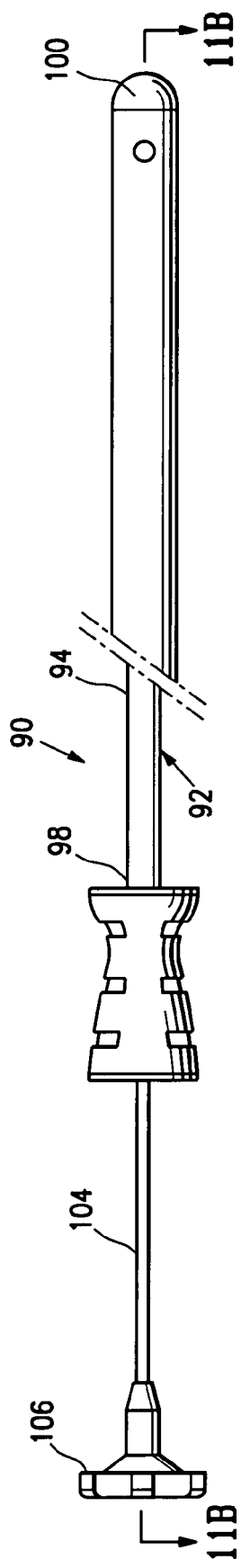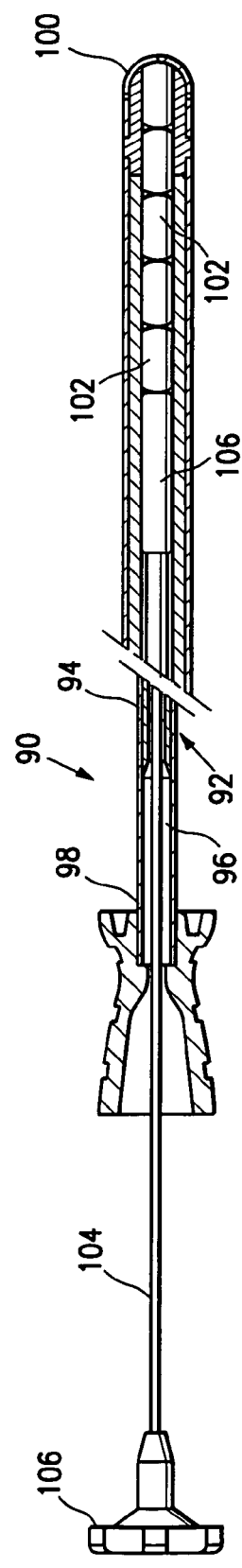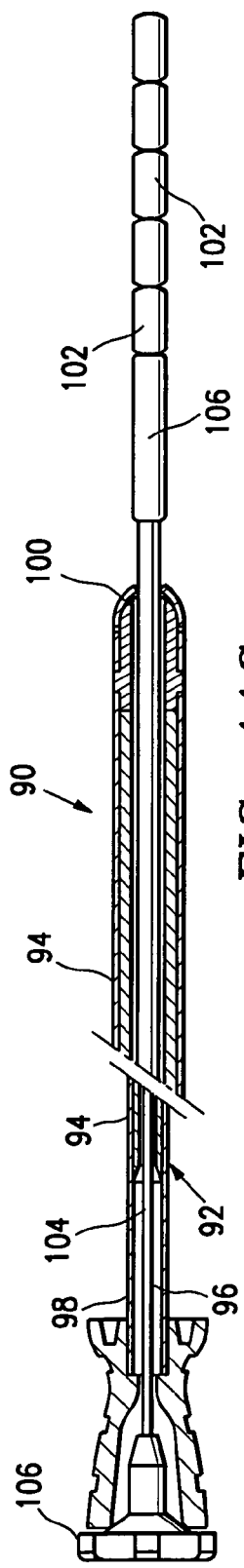

MARKER DELIVERY SYSTEM WITH OBTURATOR

FIELD OF THE INVENTION

This invention relates generally to the field of medical devices and methods. In particular, the invention relates to devices and methods for marking a biopsy site.

BACKGROUND OF THE INVENTION

In modern medical practice small tissue samples, known as biopsy specimens, are often removed from tumors, lesions, organs, muscles and other tissues of the body. Such removal of tissue samples may be accomplished by open surgical technique (i.e., removal of a small sample of tissue through a small surgical incision using a local anesthetic), or through the use of a specialized biopsy instrument such as a biopsy needle. After the tissue samples have been removed, they are typically subjected to diagnostic tests or examinations such as a) gross and microscopic examination to determine cytology and/or histology, b) biochemical analyses to determine the presence or absence of chemical substances which indicate certain disease states, c) microbiological culturing to determine the presence of bacteria or other microbes, and/or d) other diagnostic procedures. The information obtained from these diagnostic tests and/or examinations can then be used to make or confirm diagnoses and/or to formulate treatment plans for the patient.

When performing an image guided biopsy procedure an obturator is used as a place holder and is placed in tissue such that its tip will be located at the point in the patient's body where the biopsy is to be taken or where a biopsy site marker or tissue marker is to be placed after a biopsy procedure. Subsequent images are acquired that can confirm the correct placement of the obturator. When the obturator is placed at the desired location within the body, blood can enter the lumen of the obturator prior to delivery of the tissue markers. This backflow of blood into the obturator creates a risk of blood clotting.

Current obturators are constructed of homogeneous materials. During magnetic resonance imaging (MRI) guided biopsies, the tip of the obturator is located by indexing through many cross sectional views (typically every 2 mm, but higher and lower discriminations are possible). The material of the obturator will be distinguishable in the cross sectional images to a varying degree depending on the morphology of the tissue and the obturator's own material makeup. Since the obturator is homogeneous, the signature of the obturator will not vary from one cross-sectional image to the next along its length. The tip of the obturator is located by selecting the first cross-sectional image in which the obturator is not seen. This result can be visually ambiguous depending on the relative strength of the image signature of the obturator compared to the surrounding tissue.

After the biopsy sample is taken, it may take several days or weeks before the results of the examination of the sample are obtained, and still longer before an appropriate treatment decision is reached. If the decision involves surgery it is clearly important for the surgeon to find the location in the breast from where the tumor tissue has been taken in the biopsy procedure, so that the entire tumor and possibly surrounding healthy tissue can be removed.

However, radiographically imageable tissue features, originally detected in a mammogram, may be removed, altered or obscured by the biopsy procedure. In order for the surgeon or radiation oncologist to direct surgical or radiation treatment to the precise location of the breast lesion several days or weeks after the biopsy procedure was performed, it is desirable that one or more biopsy site markers be placed in or on the patient's body to serve as a landmark for subsequent location of the lesion. The purpose of such markers is to facilitate the surgical procedure that is performed while the marker is detectable.

The present invention provides a marker delivery device and method for placing an obturator at the desired site in a patient's body as a placeholder and for delivering such markers into the biopsy cavity.

SUMMARY OF THE INVENTION

This invention relates to devices and methods for placement of an intracorporeal object that functions as a marker, a therapeutic agent or a diagnostic agent and particularly for placing an obturator at a desired location within a patient's body and for delivering one or more intracorporeal objects through the obturator to that location. The obturator may operate as a place-holder during an image guided procedure such as a biopsy. The distal end of the obturator is placed where the procedure is to be performed or one or more intracorporeal objects or bodies are to be delivered.

In one embodiment having features of the present invention the device includes an obturator which has an elongated shaft with a internal lumen, a proximal end, and a substantially sealed distal end which prevents or minimizes the backflow of body fluids, such as blood, though the lumen of the obturator. The substantially sealed distal end can be a penetratable membrane or may have petals or a duckbill-type valve which are configured to allow passage of one or more intracorporeal objects or a delivery tube with one or more intracorporeal objects therethrough while preventing or minimizing entry of body fluids into the inner lumen of the obturator. Preferably the obturator is configured to fit within a procedure cannula, e.g. a cannula of a biopsy device, for example, the cannula of SenoRx's EnCor™ Magnetic Resonance Imaging Breast Biopsy System. The cannula provides access to the desired location within the patient's body.

The delivery tube has a delivery lumen configured to contain one or more intracorporeal objects. The distal tip is configured to penetrate the substantially sealed distal end of the obturator so that the intracorporeal bodies can be delivered while the obturator is in place within the body. The shape of the distal tip may be sharp or needle like when the sealed distal end of the obturator has a membrane or it may be blunt or rounded when the distal end of the obturator is petalled or has a one-way valve.

The device preferably further includes a plunger having an elongated shaft with a proximal portion and a distal portion. The plunger is configured to be slidably disposed within the lumen of the delivery tube and is located proximal to the one or more intracorporeal objects within the lumen thereof. When the plunger is extended distally within the lumen, the distal end thereof moves one or more intracorporeal objects toward and eventually through the distal end of the delivery tube. The plunger preferably has an enlarged proximal end to prevent the distal portion of the plunger from advancing too far within the delivery lumen. Alternatively, a fluid maybe used to advance the intracorporeal objects through the opening.

A method for delivering one or more intracorporeal objects to a site within a patient's body includes providing the above described device. The obturator is placed at a desired location within a patient's body. The delivery tube is advanced distally within the obturator until the distal tip passes through the substantially sealed distal end of the obturator. Next the plunger is advanced distally within the delivery tube so that at least one intracorporeal object is pushed though the opening of the distal tip.

In one embodiment of the device the distal portion of the obturator includes a detectable element capable of producing a significant image signature at the location in the patient's body where the distal portion of the obturator is placed. Preferably this embodiment includes an obturator having an elongated shaft, a proximal end, a substantially sealed distal end, and a detectable element, preferably in the form of a ring at or near the distal end. A detectable element capable of producing a significant image signature is located adjacent to the substantially sealed distal end, preferably in the form of ring at the junction between the distal tip and the elongated shaft.

The devices, systems, and methods of the present invention offer improved delivery by minimizing the backflow of body fluids, such as blood, though the obturator lumen and thereby decreasing a risk of clot formation in the obturator. These and other advantages of the invention will become more apparent from the following detailed description when taken in conjunction with the accompanying drawings.

BRIEF DESCRIPTION OF THE DRAWINGS

FIG. 2B is rotated 90° with respect to FIG. 2A.

FIG. 2C is a longitudinal cross sectional view taken along lines 2C-2C in FIG. 2A.

FIG. 2D is a transverse cross sectional view taken along lines 2D-2D in FIG. 2A.

FIG. 7B is rotated 90° with respect to FIG. 7A.

FIG. 8B is rotated 90° with respect to FIG. 8A.

FIG. 9B is rotated 90° with respect to FIG. 9A.

FIG. 10A is an elevational view of an obturator embodying features of the invention including a detectable element.

FIG. 10B is a cross sectional view of the obturator shown in FIG. 10A taken along line 10B-10B.

FIG. 10C is an enlarged view of Section 10C in FIG. 10A.

FIG. 10D is a longitudinal cross sectional view of the distal end of the obturator taken along line 10D-10D in FIG. 10C.

FIG. 10E is an enlarged view of section 10E shown in FIG. 10D.

FIG. 11A is an elevational view of an obturator embodying features of the invention including a plurality of detectable elements or bodies within the obturator.

FIG. 11B is a longitudinal cross-sectional view of the obturator shown in FIG. 11A taken along line 11B-11B.

FIG. 11C is a longitudinal cross-sectional view of the obturator as in FIG. 11B with the plunger distally advanced to discharge the detectable elements or bodies within the obturator.

DETAILED DESCRIPTION OF THE INVENTION

Figure 1A:
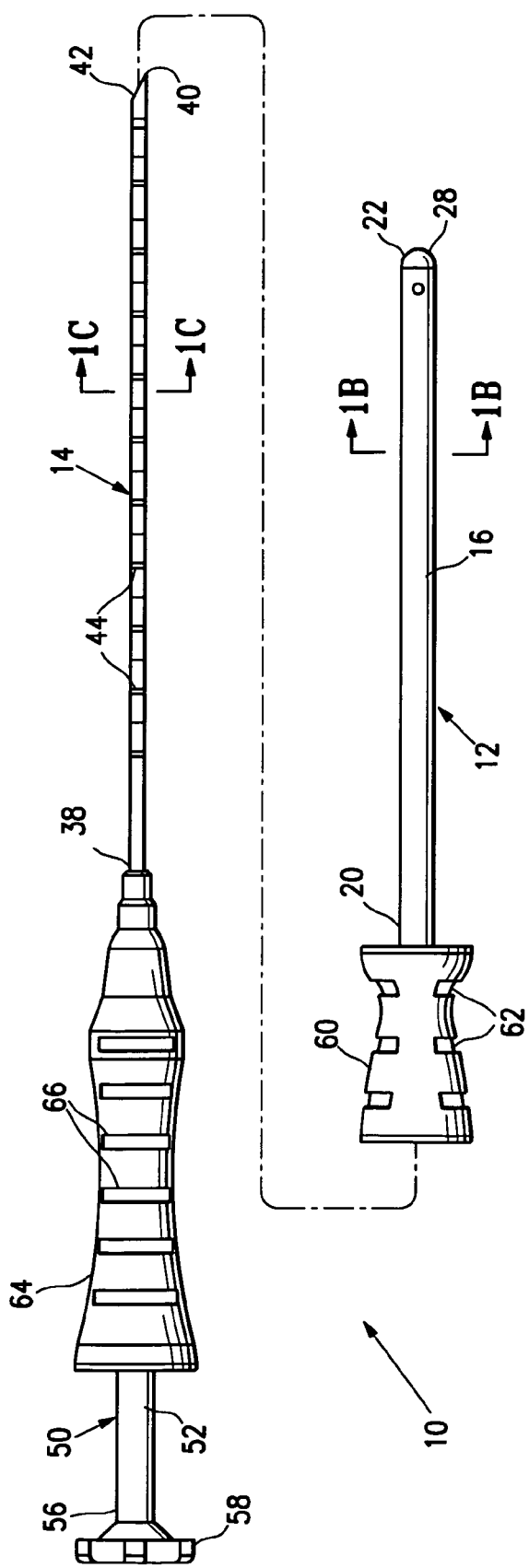
FIG. 1A is an elevational view of an assembly having features of the invention including a marker delivery shaft and an obturator.
Figure 1C:
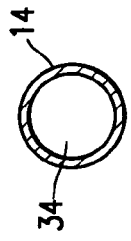
FIG. 1C is a transverse cross sectional view of the marker delivery shaft of FIG. 1A taken along lines 1C-1C.
Figure 1B:
FIG. 1B is a transverse cross sectional view of the obturator of FIG. 1A taken along line 1B-1B.
Figure 2A:
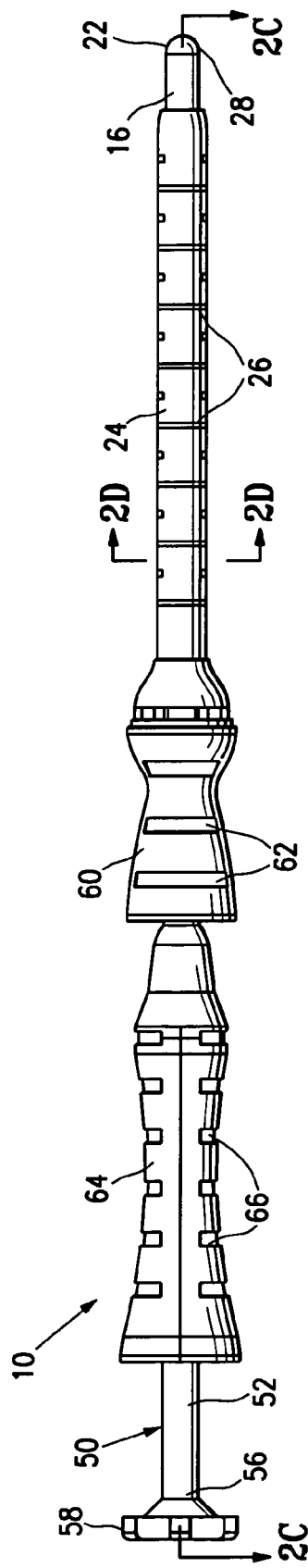
FIGS. 2A and 2B are elevational views of a delivery device embodying features of the invention wherein the distal tip of the marker delivery shaft is proximal to the substantially sealed distal end.
Figure 2B:
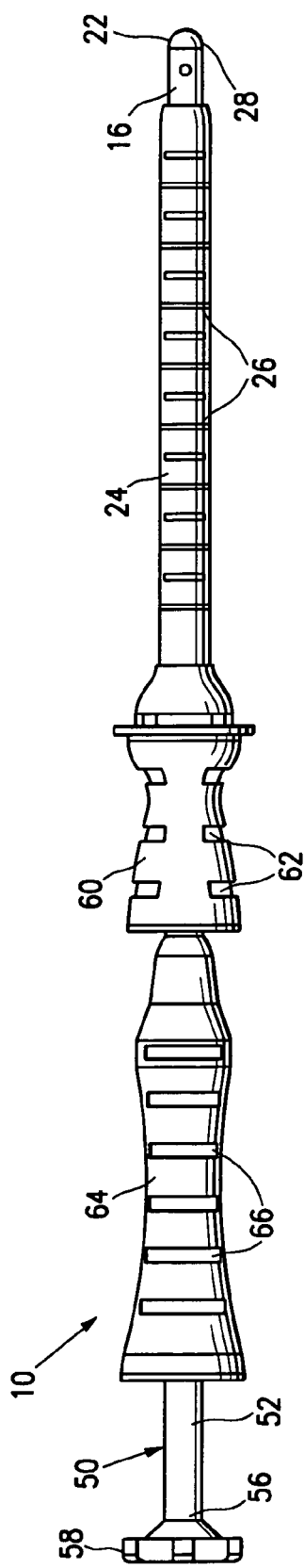

FIGS. 1A-2D shows an embodiment of a marker delivery device 10 having features of the invention including an obturator 12 and a marker delivery tubular shaft 14. The obturator 12 has an elongated shaft 16, an internal lumen 18, a proximal end 20 and a substantially sealed distal end 22. Preferably, as shown in FIGS. 2A-2D, the obturator 12 is configured to fit within a cannula 24 of a biopsy device, such as SenoRx's EnCor™ Magnetic Resonance Imaging (MRI) Breast Biopsy System. The cannula 24 provides access to the desired location within a patient's body. In some embodiments the cannula 24 includes depth markings 26 which indicate the distance which the obturator 12 has advanced within the patient's body.

Figure 3:
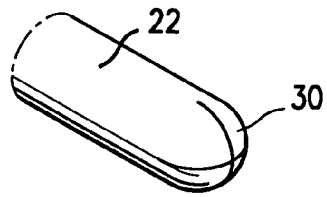
FIG. 3 is a perspective view of a substantially sealed distal end of an obturator having one or more petals.
Figure 4:
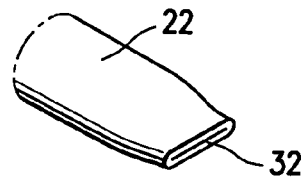
FIG. 4 is a perspective view of a substantially sealed distal end of an obturator having a duck billed valve.

The substantially sealed distal end 22 of the obturator 12 is configured to prevent or minimize the backflow of fluids, such as body fluids, through the internal lumen 18 of the obturator 12. Preferably the substantially sealed distal end 22 is formed of a penetratable membrane 28. Alternatively the substantially sealed distal end 22 is formed of two or more petals 30 (FIG. 3) or can be formed of a duck-billed valve 32 (FIG. 4).

The marker delivery tubular shaft 14 is configured to be slidably disposed within the internal lumen 18 of the obturator 12. The tubular shaft 16 has a marker delivery lumen 34 configured to contain one or more tissue markers 36 for marking a biopsy site, a proximal end 38, and a distal tip 40 with an opening 42 for passage of one or more of the markers 36. The tissue markers 36 may be those described in U.S. Pat. Nos. 6,996,433, 6,993,375, 6,862,470, 6,725,083, 6,662,041, 6,567,689, 6,427,081, 6,347,241, 6,161,034, U.S. patent application Ser. No. 10/444,770, U.S. patent application Ser. No. 10/444,428, and U.S. patent application Ser. No. 10/001,043, which are hereby incorporated by reference. The marker delivery tubular shaft 14 preferably also includes depth markings 44 which indicate the distance which the tubular shaft 14 has advanced within the obturator 12.

Figure 5:
FIG. 5 is an elevational view of a distal tip of a marker delivery tubular shaft having a needle-like shape.
Figure 6:
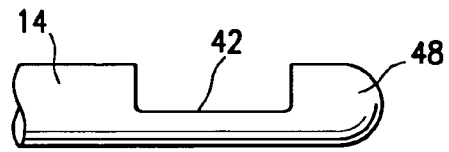
FIG. 6 is an elevational view of a distal tip of a marker delivery tubular shaft having a blunt end.

The distal tip 40 of the marker delivery shaft 14 is configured to penetrate the substantially sealed distal end 22 of the obturator 12 so that tissue markers 36 can be delivered while the obturator 12 is in place within the patient's body. Preferably the distal tip 40 is needle shaped 46 (FIG. 5), however, the distal tip can alternatively be a blunt tip 48 (FIG. 6) which is capable of penetrating a substantially sealed distal end 22 that is formed of a penetratable membrane 28 which is weakened or a distal end 22 with petals 30 or a valve 32.

Preferably the marker delivery device 10 also includes a plunger 50 having an elongated shaft 52 with a distal end 54 and a proximal end 56. The plunger 50 is configured to be slidably disposed within the marker delivery lumen 34 and is located proximal to the one or more tissue markers 36 within the marker delivery lumen 34. When the plunger 50 is extended distally within the marker delivery lumen 34 it moves one or more tissue markers toward and eventually through the opening 42 in the distal tip 40 of the marker delivery shaft 14. The plunger 50 preferably has an enlarged proximal end 58 to prevent its entry into the lumen 34. Alternatively, a fluid (not shown) may be used to advance the markers 36 through the opening 42 in the distal tip 40 of the marker delivery tubular shaft 14.

Figure 7A:
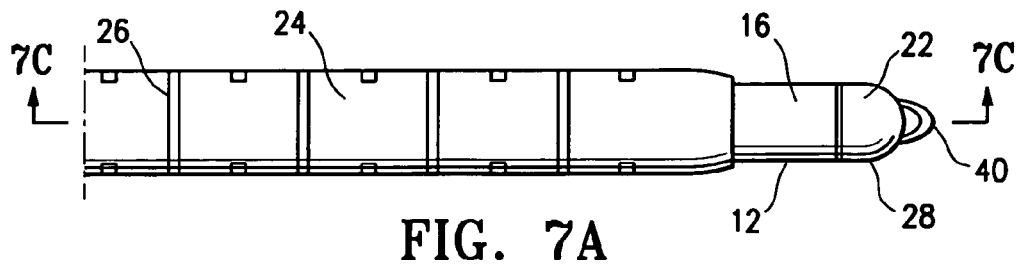
FIGS. 7A and 7B are elevational views of a distal portion of an obturator embodying features of the invention wherein the distal tip of the marker delivery shaft has partially punctured the substantially sealed distal end of the obturator and the plunger is not yet deployed.
Figure 7B:
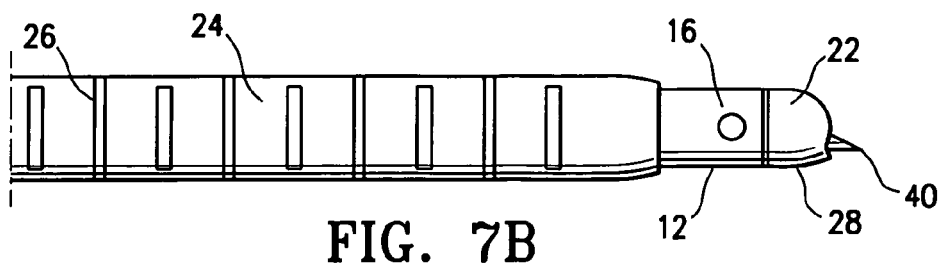
Figure 7C:
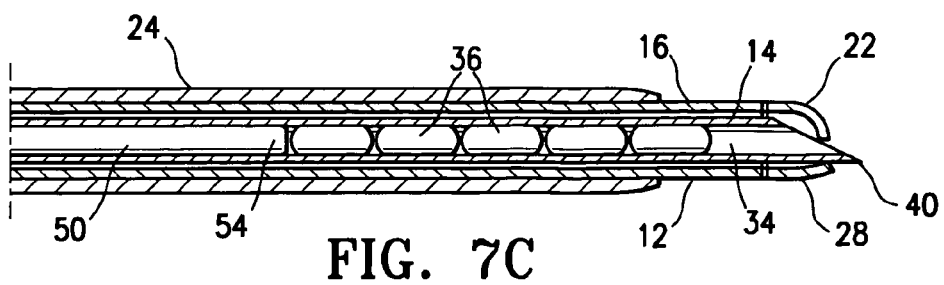
FIG. 7C is a longitudinal cross sectional view taken along line 7C-7C in FIG. 7A.
Figure 8A:
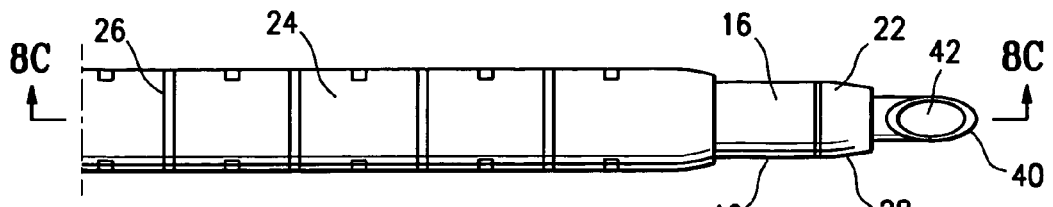
FIGS. 8A and 8B are elevational views of a distal portion of an obturator embodying features of the invention wherein the distal tip of the marker delivery shaft has completely punctured the substantially sealed distal end of the obturator and the plunger is not yet deployed.
Figure 8B:
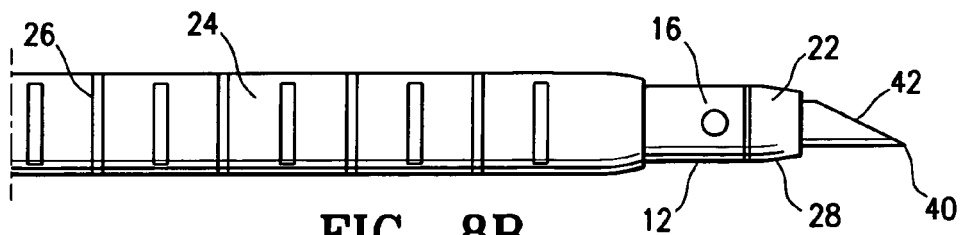
Figure 8C:
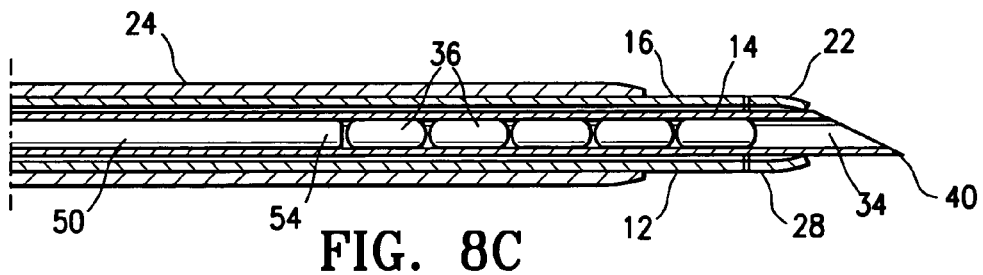
FIG. 8C is a longitudinal cross sectional view taken along lines 8C-8C in FIG. 8A.
Figure 9A:
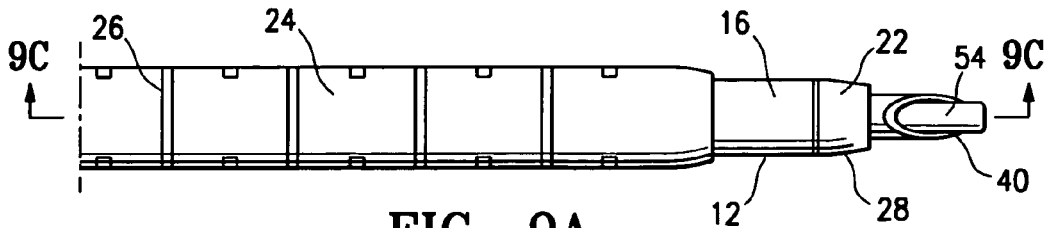
FIGS. 9A and 9B are elevational views of a distal portion of an obturator embodying features of the invention wherein the distal tip of the marker delivery shaft has completely punctured the substantially sealed distal end of the obturator and the plunger is deployed.
Figure 9B:
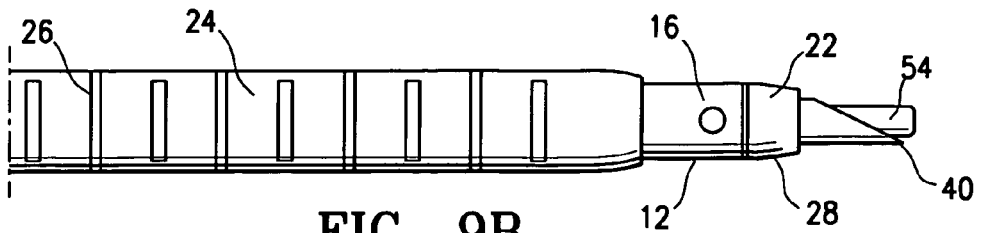
Figure 9C:
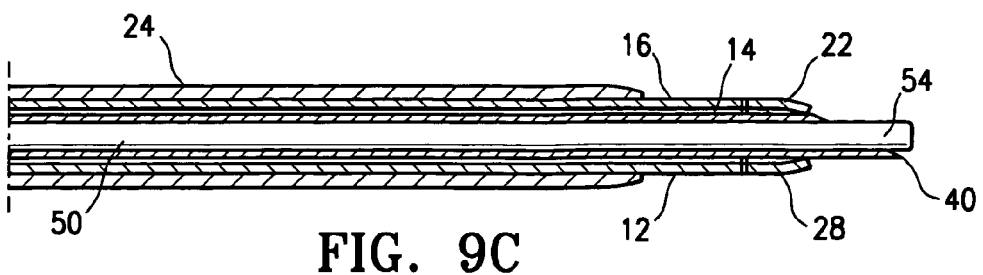
FIG. 9C is a longitudinal cross sectional view taken along line 9C-9C in FIG. 9A.

FIGS. 7A-7C show the distal tip 40 of the marker delivery tube 14 partially penetrating the substantially sealed distal end 22 of the obturator 12. The tissue markers 36 in FIG. 7A-7C are contained within the marker delivery lumen 34. FIGS. 8A-8C show the distal tip 40 completely penetrating the substantially sealed distal end 22 of the obturator 12 and the tissue markers 36 within the marker delivery lumen 34. FIGS. 9A-9C show the distal tip 40 of the marker delivery tubular shaft 14 completely penetrating the substantially sealed distal end 22. In FIGS. 9A-9C the plunger 50 is deployed distally within the marker delivery lumen 34.

Preferably the obturator 12 has a hub 60 at the proximal end 20 of the obturator shaft 16. The hub 60 may have gripping ridges 62 which allow a person operating the device 10 to maintain a grip on the device 10. The marker delivery tubular shaft 14 preferably also has a hub 64 at the proximal end of the marker delivery shaft 38 with gripping ridges 66. At least a portion of the hub 64 of the marker delivery tubular shaft 14 is configured to fit within the hub 64 of the obturator 12 when the marker delivery shaft 14 is inserted into the obturator 12.

The marker delivery device 10 is preferably formed of a non-magnetic material. A plastic such as MAKROLON®, a polycarbonate from Bayer Material Sciences a division of Bayer AG, is suitable and will not interfere with a magnetic resonance imaging device (MRI). The device may also include a radiopaque material which allows for detection of the device. Alternatively the location of the obturator 12 may be determined by detecting air within the elongated shaft 16 of the obturator 12 with a magnetic resonance imaging device (not shown).

A method for delivering a tissue marker to a site within a patient's body includes providing the above described device. The obturator 12 of the device 10 is inserted into a desired location within a patient's body. Preferably the obturator 12 is placed within the cannula 24 of a biopsy device that remains in the patient's body after the biopsy device is removed. The marker delivery tubular shaft 14 is then inserted into the obturator 12 and the distal tip 40 of the tubular shaft 14 is advanced through the substantially sealed distal end 22 of the obturator 12. At least one tissue marker 36 within the marker delivery tubular shaft 14 is then advanced distally through the opening 42 in the distal tip 40 of the marker delivery tubular shaft 14. Preferably a plunger 50 is advanced distally within the tubular shaft 14 so that at least one tissue marker 36 is moved through the opening 42 in the distal tip 40. Alternatively a fluid (not shown) can be used in place of the plunger to move the tissue markers 36 through the distal tip 40.

An embodiment of the device having features of the invention, which is shown in FIGS. 10A-10G, includes an obturator 68 having an elongated shaft 70 including a cylindrical wall with an internal lumen 72, a proximal end 74, a substantially sealed distal end 76, and a detectable element 78 capable of producing a relatively significant image signature. Preferably the detectable element 78 is incorporated into the obturator 68 at a location determined to be optimum for complimenting the subsequent procedure.

Figure 10F:
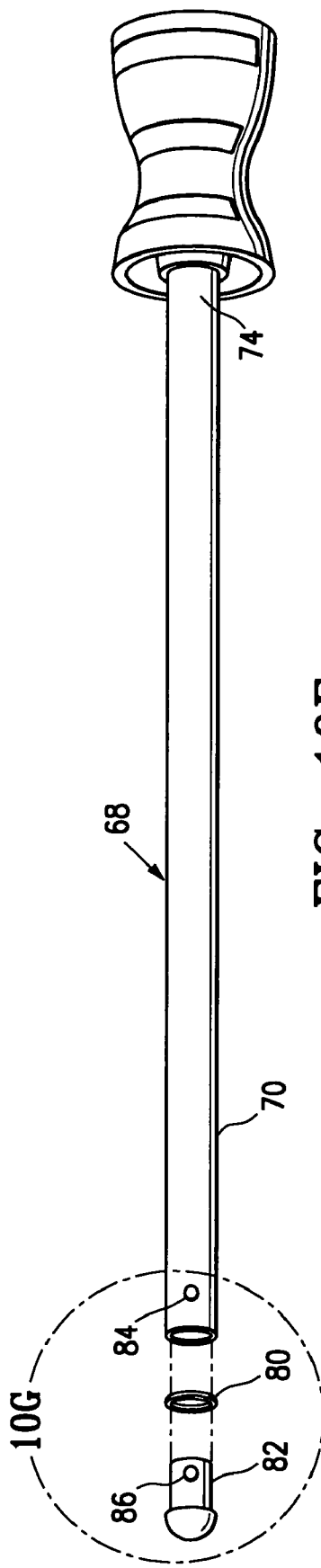
FIG. 10F is an perspective view of the obturator wherein the distal end of the obturator, the detectable element, and the proximal portion of the obturator are shown separated.
Figure 10G:
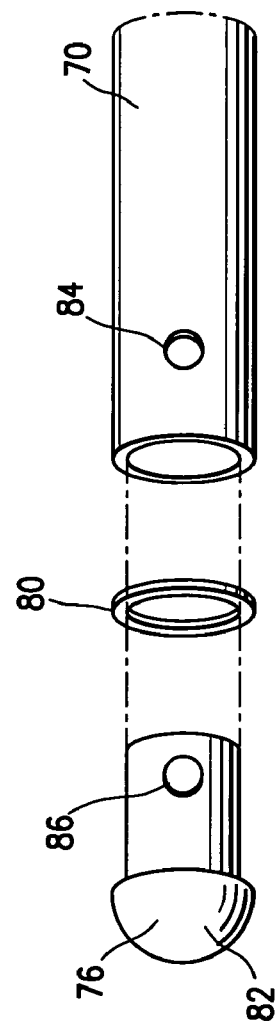
FIG. 10G is an enlarged view of Section 10G shown in FIG. 10F.

As shown in FIG. 10G, the detectable element 78 preferably is in the form of a ring 80 located near the substantially sealed distal end 76 of the obturator 68. Preferably the substantially sealed distal end 76 of the obturator 68 is located on an obturator tip 82. As shown in FIGS. 10A, 10C, 10F and 10G, the detectable element 78/80 is in contact with the mating surfaces of a terminal distal end of the cylindrical wall of the elongated shaft 70 and the obturator tip 82. The cylindrical wall of the elongated shaft 70 also includes at least one aperture 84 and the obturator tip 82 of the obturator 68 preferably includes a raised tab 86 which extends into the aperture 84 to hold the obturator tip 82 in place. The detectable element 78 in ring form 80 may be placed at the point where the obturator tip 82 and the elongated shaft 70 of the obturator 68 meet, i.e., at the junction between the obturator tip 82 and the terminal distal end of the cylindrical wall of the elongated shaft 70 of the obturator 68.

Preferably the detectable element 78 is in a form which allows the internal lumen of the obturator 72 to remain unobstructed, such as a ring 80. The detectable element 78 can also be a small sphere or rod, one or more wires, or a collar. Also any plan-form shape constructed of sheet material, either planar or formed into a non-planar shape. Alternatively, the detectable element 78 may be the entire tip 82 of the obturator 68. Alternatively more than one detectable element 78 could be incorporated into the obturator 68 to be used as a marker capable of determining the depth of the obturator 68 within a patient's body (not shown).

FIGS. 11A-C illustrate an alternative embodiment of an object delivery device 90 having features of the invention including an obturator 92 which has an elongated shaft 94, an internal lumen 96, a proximal end 98 and a substantially sealed distal end 100. Preferably, as previously discussed with the other embodiments, the obturator 92 is configured to fit within a cannula of a biopsy device, such as SenoRx's EnCor™ Magnetic Resonance Imaging (MRI) Breast Biopsy System. The substantially sealed distal end 100 of the obturator 92 is configured to prevent or minimize the backflow of fluids, such as body fluids, through the inner lumen 96. A plurality of intracorporeal objects 102, e.g. biopsy site markers, are disposed within the inner lumen 96. A plunger 104 with an enlarged head 106 is slidably disposed in part within the inner lumen 96 proximal to the plurality of intracorporeal objects 102. Distal movement of the plunger 104 pushes the objects 102 through the distal end into a body site. In this embodiment, the intracorporeal objects may not be able to penetrate a membrane, so the substantially sealed distal end 100 may be formed of two or more petals such as shown in FIG. 3 or can be formed of a duck-billed valve such as shown in FIG. 4.

Suitable materials for use as the detectable element 78 are metal, ceramic, metal filled plastic, mineral filled plastic, or a radiopaque material. Radiopaque materials such as stainless steel, platinum, gold, iridum, tantalum, tungsten, silver, rhodium, nickel, bismuth or other radiopaque metals, mixtures of radiopaque metals, oxides of radiopaque metals, barium salts, iodine salts, iodinated materials, and combinations thereof are suitable as well. Additionally, MRI contrast agents such as Gadolinium and vitamin E may also be employed.

If desired, an imageable stylet may be used within the inner lumen of the sealed obturator to show the axis of the instrument and the depth of the insertion within the body. Preferably the stylet is formed of material which is compatible with MRI and which is seen in MRI generated images. Suitable materials include non-magnetic metals, non-magnetic metal filled plastics, hollow tubes filled at least in part with an MRI visible substance such as Gadolinium or other fluids.

While particular forms of the invention have been illustrated and described herein directed to detectable markers, it will be apparent that various modifications and improvements can be made to the invention. For example, the deployed bodies may be therapeutic or diagnostic agents in addition to or in lieu of being markers. Moreover, individual features may be shown or otherwise described in one embodiment and not in others, but those skilled in the art will recognize that individual features of one embodiment of the invention can be combined with any or all the features of another embodiment. Accordingly, it is not intended that the invention be limited to the specific embodiments illustrated.

Terms such as "element", "member", "component", "device", "means", "portion", "section", "steps", and words of similar import when used herein shall not be construed as invoking the provisions of 35 U.S.C. §112(6) unless the following claims expressly use the term "means" followed by a particular function without reference to a specific structure or the term "step" followed by a particular function without reference to a specific action. All patents and all patent applications referred to above are hereby incorporated by reference in their entirety.

What is claimed is:

1. An obturator, comprising:
   a. an elongated shaft comprising a cylindrical wall having a proximal end, a distal end and defining an internal lumen extending to the distal end and an obturator tip secured to the distal end; and
   b. a detectable element which is in contact with the mating surfaces of the terminal distal end of the cylindrical wall and the obturator tip, said detectable element comprising a material selected from the group consisting of metal, ceramic, metal-filled plastic, a radiopaque material, or a mineral-filled plastic and being configured to produce a significant magnetic resonance image signature.

2. The obturator of claim 1 wherein the distal end of the cylindrical wall has at least one aperture and the obturator tip has at least one raised tab configured to fit within said at least one aperture.

3. The obturator of claim 1 wherein the detectable element is a ring which is disposed at the junction between the obturator tip and the distal end of the cylindrical wall of the elongated shaft of the obturator.

* * * * *